(12) United States Patent
Budai et al.

(10) Patent No.: US 8,746,929 B2
(45) Date of Patent: Jun. 10, 2014

(54) DEVICE WITH COMBINED FEATURES OF LIGHTING AND AIR PURIFICATION

(75) Inventors: Miklós Budai, Nagykörös (HU); László Balázs, Godollo (HU); István Deme, Budapest (HU)

(73) Assignee: GE Lighting Solutions, LLC, Cleveland, OH (US)

( * ) Notice: Subject to any disclaimer, the term of this patent is extended or adjusted under 35 U.S.C. 154(b) by 132 days.

(21) Appl. No.: 13/273,371

(22) Filed: Oct. 14, 2011

(65) Prior Publication Data

US 2013/0094204 A1 Apr. 18, 2013

(51) Int. Cl.
*F21V 9/00* (2006.01)
*F21V 29/00* (2006.01)

(52) U.S. Cl.
USPC ................ 362/253; 362/249.02; 362/249.11; 362/157

(58) Field of Classification Search
USPC .......................... 362/253, 157, 184, 267, 373
See application file for complete search history.

(56) References Cited

U.S. PATENT DOCUMENTS

| | | | | |
|---|---|---|---|---|
| 2,485,410 | A * | 10/1949 | Pope | 250/429 |
| 6,939,611 | B2 | 9/2005 | Fujishima et al. | |
| 7,083,659 | B1 * | 8/2006 | Joyce et al. | 55/385.1 |
| 7,175,911 | B2 * | 2/2007 | Zhou et al. | 428/403 |
| 7,524,793 | B2 | 4/2009 | Orth-Gerber et al. | |
| 7,585,344 | B2 * | 9/2009 | Paterson et al. | 55/413 |
| 7,699,501 | B2 * | 4/2010 | Liu | 362/294 |
| 7,914,733 | B2 * | 3/2011 | Carey | 422/5 |
| 2002/0033327 | A1 * | 3/2002 | Benda et al. | 204/158.2 |
| 2005/0109708 | A1 | 5/2005 | Sheehan | |
| 2006/0280660 | A1 | 12/2006 | Weiss | |
| 2007/0230181 | A1 | 10/2007 | Fujishima et al. | |
| 2009/0041632 | A1 | 2/2009 | Day et al. | |
| 2009/0049985 | A1 * | 2/2009 | Leroux et al. | 95/79 |
| 2009/0059559 | A1 | 3/2009 | Pabst et al. | |
| 2009/0097243 | A1 | 4/2009 | Lan et al. | |
| 2009/0244895 | A1 | 10/2009 | Chen | |

(Continued)

FOREIGN PATENT DOCUMENTS

| CN | 1494458 | 5/2004 |
|---|---|---|
| CN | 21187759 Y | 1/2009 |

(Continued)

OTHER PUBLICATIONS

Machine English transaltion of JP 2006289215 to Kikuhara et al.*

*Primary Examiner* — Sikha Roy
(74) *Attorney, Agent, or Firm* — Fay Sharpe LLP

(57) ABSTRACT

A lighting device combined with an air purification feature is disclosed. At least one function of the device is to provide high quality directional light for general lighting purposes. An additional function is to decompose VOCs and/or destroy microbes in the ambient air. The heat generated by white LEDs is utilized to generate air flow through the device. The geometry is designed to utilize the chimney effect and maximize volumetric flow. The circulated air is purified by a photocatalytic layer applied to the interior surface of the device. The lighting device can be built into pendant luminaires or lamps, thus ensuring vertical orientation of the light module. The exemplary embodiments may be applied in public places, hospitals, ward rooms, and other locations where a cost effective disinfection method is needed.

20 Claims, 12 Drawing Sheets

(56) References Cited

U.S. PATENT DOCUMENTS

| | | |
|---|---|---|
| 2009/0251898 A1 | 10/2009 | Kinnune et al. |
| 2009/0268463 A1 | 10/2009 | Huang et al. |
| 2009/0291029 A1 | 11/2009 | Ogasawara et al. |
| 2009/0316400 A1* | 12/2009 | Kuo et al. .................... 362/235 |
| 2010/0079998 A1 | 4/2010 | Mrakovich et al. |
| 2010/0238658 A1* | 9/2010 | Xiang et al. ................. 362/235 |
| 2011/0063849 A1 | 3/2011 | Alexander et al. |

FOREIGN PATENT DOCUMENTS

| | | |
|---|---|---|
| EP | 2012356 | 1/2009 |
| EP | 2028417 | 2/2009 |
| JP | 10041552 | 2/1998 |
| JP | 10149708 | 6/1998 |
| JP | 10233190 | 9/1998 |
| JP | 10321191 | 12/1998 |
| JP | 11333304 | 12/1999 |
| JP | 2000325799 | 11/2000 |
| JP | 2002102654 | 4/2002 |
| JP | 2003208809 | 7/2003 |
| JP | 2004000663 | 1/2004 |
| JP | 2004335377 | 11/2004 |
| JP | 2006116415 A * | 5/2006 |
| JP | 2006216574 | 8/2006 |
| JP | 2006289215 A * | 10/2006 |
| JP | 2007061765 | 3/2007 |
| JP | 2009163955 | 7/2009 |
| WO | WO 02053284 | 7/2002 |
| WO | WO 02102497 A1 * | 12/2002 |
| WO | WO 2007/145184 | 12/2007 |
| WO | WO 2008/137732 | 11/2008 |
| WO | WO 2009/084372 | 7/2009 |
| WO | WO 2009/110993 | 9/2009 |
| WO | WO 2009/113045 | 9/2009 |
| WO | WO 2009/123752 | 10/2009 |

* cited by examiner

DEVICE WITH COMBINED FEATURES OF LIGHTING AND AIR PURIFICATION

BACKGROUND

The present exemplary embodiment relates generally to lighting. It finds particular application in conjunction with light emitting diodes (or LEDs) that may be used for general lighting and air purification and will be described with particular reference thereto. However, it is to be appreciated that the present exemplary embodiment is also amenable to other like applications.

By way of background, air quality is a health concern, especially in frequently visited public places, such as hospitals and schools. With regard to disinfecting the air in such places, air purifiers have been used to decompose toxic volatile organic compounds (VOCs) and living organisms like bacteria and viruses. Current solutions, such as air filtration or UV (ultraviolet) lamp irradiation, however, require forced air circulation by means of fans and motors. And direct UV illumination is not always possible in occupied places. Therefore, alternative sources have been contemplated.

Recently, light emitting diode (LED) lamps have been employed for various lighting applications. LED lamps are preferred because they consume less power (watts) than their fluorescent and incandescent counterparts, which results in an energy savings.

Thus, there is a need for a lighting device combined with an air purification feature, which does not, for example, use harmful UV radiation or incorporate a fan.

BRIEF DESCRIPTION

An improved LED lighting device with an air purification feature is disclosed herein. At least one function of the device is to provide high quality directional light for task lighting, accent lighting, and/or general lighting purposes. An additional function of the device is to decompose VOCs and/or destroy microbes in the ambient air. The heat generated by white LEDs is utilized to generate air flow through the device. The geometry of the device is designed to utilize the chimney effect and maximize volumetric flow. The circulated air may be purified, for example, by a photocatalytic layer applied to the interior surface of the device. The lighting device can be built into pendant luminaires or lamps, for example, thus ensuring vertical orientation of the light module. The exemplary embodiments may be applied in public places, hospitals, ward rooms, horticultural environments (e.g., greenhouses), livestock growing places (e.g., stables) and other locations where a cost effective air disinfection method is needed.

In one embodiment, a lighting and air purification apparatus is provided. The apparatus includes a body having a top end and a bottom end and an interior surface coated with a photocatalytic layer for purifying air, wherein the body also includes a plurality of inlet openings spaced near the bottom end configured to draw in ambient air and at least one outlet opening at the top end configured to release heated air. The apparatus also includes a heat conductive element at the bottom end of the body and a first set of LEDs on a lower surface of the heat conductive element and a second set of LEDs on an upper surface of the heat conductive element, wherein the first set of LEDs is configured to provide light and the second set of LEDs is configured to provide light having an emission that is greater than 400 nm for air purification. The first set of LEDs may be configured to provide light between 50 and 20000 lumens.

Optionally, the body comprises a conical member and the top end of the conical member has an upper diameter that is smaller than a lower diameter of the bottom end of the conical member. In that case, the outlet opening may comprise a round hole and the inlet openings may comprise round holes spaced radially around the bottom end of the conical member. Or the outlet opening may comprise a round hole and the inlet openings may comprise rectangular openings oriented diagonally and spaced radially around the bottom end of the conical member.

The thickness of the photocatalytic layer may be configured to allow transmission of visible light. The photocatalytic layer may comprise (1) doped titanium oxide that is activated by light from the second set of LEDs, (2) single or mixed oxides of metals selected from the group of Ti, Zn, Zr, Ce, V, W, Bi—W, W—Cd, Zn—In, Bi—Cd—In, and Pb—Bi—Nb, or (3) an oxide-nitride compositions selected from the group of GaN—ZnO and $Ge_3N_4$—$RuO_2$. The photocatalytic layer may be configured to oxidize harmful organic molecules (VOCs) and destroy microbes in the ambient air drawn in through the inlet openings.

The heat conductive element may comprise a metal plate, wherein each set of LEDs is attached by screws. In addition, the heat conductive element may comprise a heat conductive plate with a metal core printed circuit board attached to each side, wherein the metal core printed circuit board on the bottom side is substantially as large as the heat conductive plate and the metal core printed circuit board on the inner side is smaller than the heat conductive plate for creating a heat bridge between the heat conductive plate and air moving inside the conical member.

The body may comprise a conical member that is transparent and the second set of LEDs may be white LEDs with a high 405 nm component. The apparatus may also include optical elements at the bottom end of the body for directing light from the first set of LEDs. The body may also comprise a linear member and include optical elements for directing light from the first set of LEDs.

In another embodiment, a lighting and air purification apparatus is provided. The apparatus includes a body having a top end and a bottom end and an interior surface coated with a photocatalytic layer for purifying air, wherein the body also includes a plurality of inlet openings spaced near the bottom end configured to draw in ambient air and at least one outlet opening at the top end configured to release heated air. The apparatus also includes a mechanical holder at the bottom end of the body that is configured to provide mechanical and electrical connection of an LED module to the body and a first set of LEDs mounted in the LED module, wherein the first set of LEDs is configured to provide light in a downward direction. The apparatus further includes a second set of LEDs mounted on an upper surface of a heat conducting element, wherein the second set of LEDs is configured to provide light in an upward direction and having an emission that is greater than 400 nm for air purification.

BRIEF DESCRIPTION OF THE DRAWINGS

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure will be set forth in the following detailed description of the disclosure when considered in conjunction with the drawings, in which.

DETAILED DESCRIPTION

Figure 1:
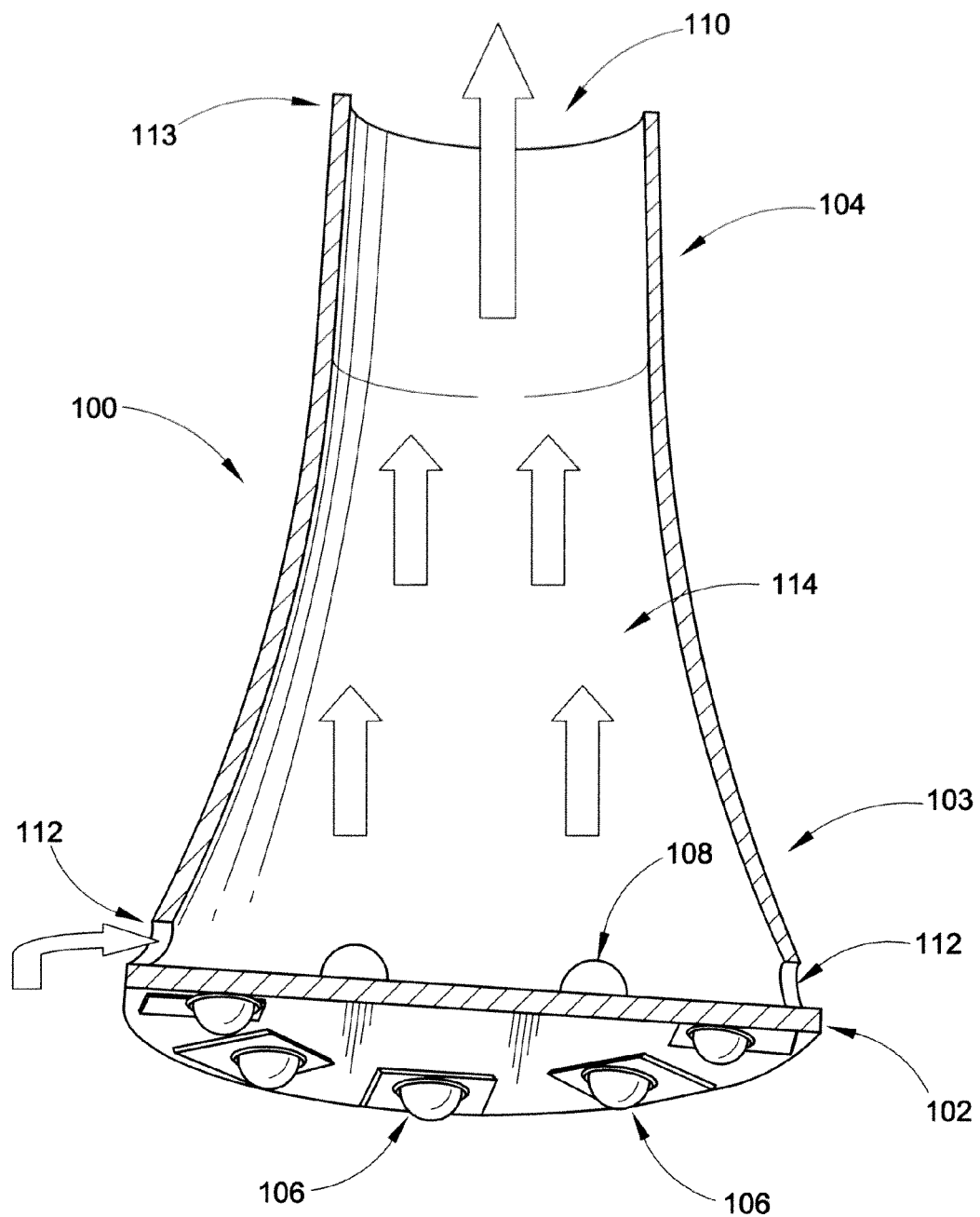
FIG. 1 is a schematic view of a preferred embodiment of a lighting device in accordance with the exemplary embodiments.

One or more embodiments or implementations are hereinafter described in conjunction with the drawings, where like reference numerals are used to refer to like elements throughout, and where the various features are not necessarily drawn to scale.

With reference to FIG. 1, a schematic view of a preferred embodiment of a lighting device 100 is shown. The lighting device 100 generally includes a heat conductive layer and/or a circuit board 102 assembled at the bottom end 103 of a body (or housing) 104, which acts as a chimney, inducing an upward flow of air in the lighting device 100. Generally, as shown in FIG. 1, the body 104 is conical in shape. However, other configurations and/or shapes may be implemented to the extent that they help to provide a chimney effect, as described more fully below.

Suitably, one or more LEDs 106 may be mounted on the lower surface of the heat conductive layer 102. The LEDs 106 can be phosphor-coated LEDs, RGB LEDs, monochromatic LEDs, or a combination of phosphor and monochromatic LEDs. The light produced by the LEDs 106 may be used for various types of lighting applications, including task lighting, accent lighting, general lighting and/or horticultural lighting. Task lighting is mainly functional and is usually the most concentrated, for purposes such as reading or inspection of materials. Accent lighting is mainly decorative, intended to highlight pictures, plants, or other elements of interior design or landscaping. General lighting fills in between the two and is intended for general illumination of an area. Indoors, this would be a basic lamp on a table (task lighting) or floor, or a fixture on the ceiling (general lighting).

There is generally no restriction regarding the number and arrangement of the LEDs, since the heat conductive layer 102 spreads any heat equally. That is, the LEDs 106 may be arranged so as to correspond to the light pattern required. Any suitable lens can be used, and the arrangement of the LEDs 106 is not limited in this application. The lighting device 100 may generally provide a minimum of 50 lumens and a maximum of 20000 lumens but preferably between 600 and 10000 lumens.

The lighting device 100 also includes one or more auxiliary LEDs 108 mounted on the upper side of the heat conductive layer 102. The auxiliary LEDs 108 generally have an emission that is greater than 400 nm and is preferably at 405 nm (violet) or 450-460 nm (blue). In the case of a transparent conical member or in indirect lighting applications, the LEDs 108 can be white LEDs with a high 405 nm component. The power consumption may be between 1 and 90% of the LEDs on the lower surface of the circuit board 106, but preferably between 1 and 20%.

The heat conductive layer 102 has at least two functions: (1) it should distribute heat generated by the LEDs (106, 108) equally, and (2) it should provide an electrical connection for the LEDs (106, 108). In FIG. 1 the heat conductive layer 102 comprises a metal plate, with each side of LEDs (106, 108) being attached by soldering, mechanical fixing or chemical bond. It is to be understood, however, that the element 102 may also comprise a heat conductive plate (e.g., aluminium, copper, etc.), and on each side a MCPCB (metal core printed circuit board) or other adequate holder (Chip on Board technology) is attached, or a holder surface can be created on the heat conductive element in such a way that LED modules can be attached in a twist and lock style creating electrical and thermal connection, or a combination of all the above mentioned methods may be employed. The attachment of the holder can be made with mechanical fixing or a chemical bond. The holder on the bottom side can be as large as the plate, since it has an effect only with respect to equal heat distribution. But for the inner side (for the photocatalytic LEDs 108) it should be smaller to help ensure the best heat bridge between the plate and the air moving inside the chimney. The holder(s) provide an electrical connection for the LEDs (106, 108), which can be serial or parallel. The LEDs (106, 108) may be attached by soldering, chemical bond, or mechanical fixing.

The LEDs (106, 108) generate heat during operation of the lighting device 100. Based on an electrical model analogy and "Ohm's Thermal Law," the relationship can be represented by the following formula:

$$T_j - T_a = R_{thja} \times (V_d \times I_d) \qquad (1)$$

where $T_j$=LED junction temperature, $T_a$=Ambient temperature, $R_{thja}$=Thermal resistance junction to ambient, $V_d$=LED forward voltage, and $I_d$=LED forward current.

The conical member 104 typically includes at least one outlet opening 110 at the upper end and a plurality of small openings (or apertures) 112 spaced near the bottom of the conical member 104. For example, as shown in FIG. 1, the inlet openings 112 may be generally round holes. However, other configurations may be implemented to the extent that they help to provide a chimney effect. For example, the inlet openings 112 may be rectangular slots oriented vertically, diagonally, and/or horizontally around the bottom end of the conical member 104.

In operation, ambient air is drawn in through a plurality of inlet openings 112 near the bottom end 103 of the conical member 104. Heated air flows upwards through a top opening 110 at the top end 113 of the conical member 104, at least in part due to the "chimney" effect. To function properly, the minimum temperature needed is approximately 35° C. with 4-5 Watts of electrical power.

It is to be understood that the "chimney" effect (also called the "buoyancy" or "stack" effect) is based on the natural tendency of the air to move from high to low pressures (natural ventilation). The warm air rises naturally, producing air movement through the building. The existence of a chimney is increasing this effect for several reasons. Due to the lower effective section, the air speed is accelerated in the chimney. Consequently, the pressure is lowering in this section (principle of energy conservation—Venturi effect). Due to the higher difference of pressure, the air movement is accelerated. The chimney creates a bigger difference in height, thus increasing the Venturi effect and also the difference in temperature from the air intake to the exhaust point. Note that the presence of wind conditions (even slight) would have the effect of lowering the pressure at the chimney exhaust and thus increasing the air extraction efficiency.

The conical member 104 has at least two functions in this device: (1) it provides a type of chimney, which directs the warm air flow in an upward direction, and (2) it provides a holding surface for a photocatalytic layer 114, which helps to create a photocatalytic effect by exposing the ambient air in the conical member 104, for example, to 405 nm light. The conical member 104 can be composed of a heat conductive material, such as metal. In that case, the air flow in the system is relatively smaller, but the cooling surface of the light source (s) is increased. Such a configuration is generally recommended for higher wattages. On the other hand, if the conical member 104 is composed of a material that is not heat conductive (for example, plastic), the air flow is increased, but the cooling surface of the light source(s) is smaller. This configuration is generally recommended for lower wattages. The material used to make the conical member 104 can be transparent (for example, glass) so that the indirect lighting of the system (i.e., the second set of LEDs) can be used for general lighting. The height of the conical member 104 shall vary depending on the total surface area of the system. More particularly, the ratio of the height of the conical member (H) to the total area of the system (A) is generally between 0.005 and 0.5.

The bottom diameter of the conical member is typically larger than the upper diameter so as to maximize the flow of air through the conical member 104. The surface area of the inlet openings 112 generally depends on the total surface area of the whole system. Thus, the ratio of the inlet hole surface area/total surface area generally has a minimum of 0.001 and a maximum of 0.4. The inlet holes 112 typically have no specific shape requirement, and they can be any combination of a semicircle, a circle, a square, a rectangle, etc.

The air stream within the conical member 104 is preferably in contact with a photocatalytic layer 114 coated on the interior surface of the conical member 104. The surface coverage of substrates by photocatalysts is above 20 ug/cm$^2$, but it is not necessarily uniform. The photocatalytic layer 114 may contain doped titanium oxide, which is activated by the light of the auxiliary LEDs 108. But other any other typical photocatalytic material can be considered, including but not limited to:

Single or mixed oxides of metals (doped or undoped): Ti, Zn, Zr, Ce, V, W, Bi—W, W—Cd, Zn—In, Bi—Cd—In, Pb—Bi—Nb Oxide-nitride compositions: GaN—ZnO, Ge$_3$N$_4$—RuO$_2$ The activated photocatalytic layer 114 suitably oxidizes harmful organic molecules (VOCs) and destroys microbes in the air.

It is noted that 405 nm is an adequate wavelength to kill bacteria/germs if the illuminated surface is coated with the photocatalytic layer 114 absorbing at 405 nm. Some bacteria can be effectively killed by a mere 405 nm irradiation without a photocatalysator.

In another embodiment the conical member 104 of the lighting device 100 is composed of a transparent material, such as glass or plastic. In this embodiment, the coating thickness of the photocatalytic layer 114 is set to allow transmission of visible light. The auxiliary LEDs 108 can be, in this case, white LEDs having a significant emission at 405 nm or 450 nm. The 405 nm or 450 nm radiation is substantially absorbed by the photocatalytic layer 114. The advantage of this embodiment is that scattered white light is emitted upwards from the conical element 104 providing indirect light, which is preferred in some lighting applications. Generally, the device 100 could still have the white LEDs on the bottom surface of the circuit board 102.

Figure 2:
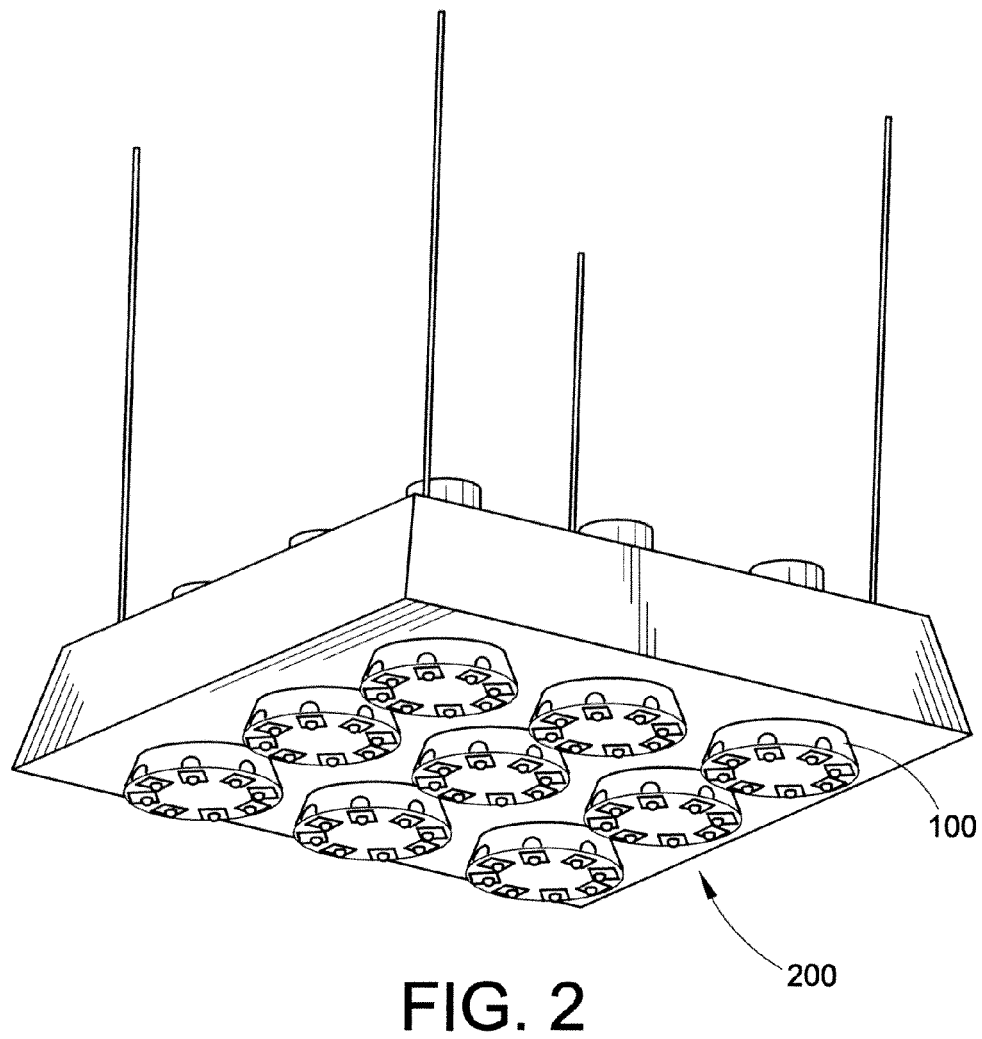
FIG. 2 is a perspective view of the lighting device incorporated into a pendant luminaire.
Figure 3:
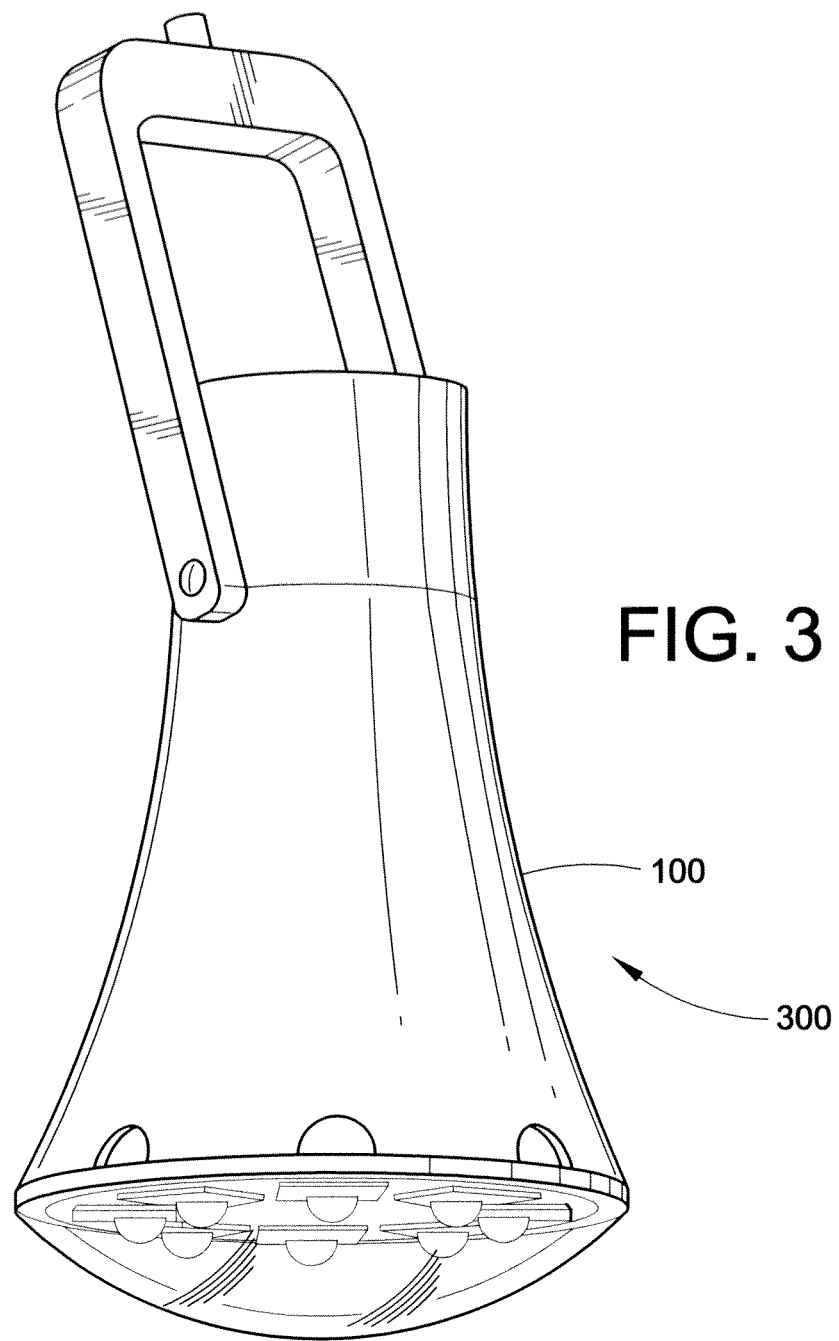
FIG. 3 is a perspective view of the lighting device incorporated into a pendant lamp.

The lighting device 100 can be incorporated into a pendant luminaire 200 (see FIG. 2) or a lamp 300 (see FIG. 3), thus ensuring vertical orientation of the lighting device 100. Generally, the lighting devices shown in FIGS. 2 and 3 would operate in the same manner as described above.

Figure 4:
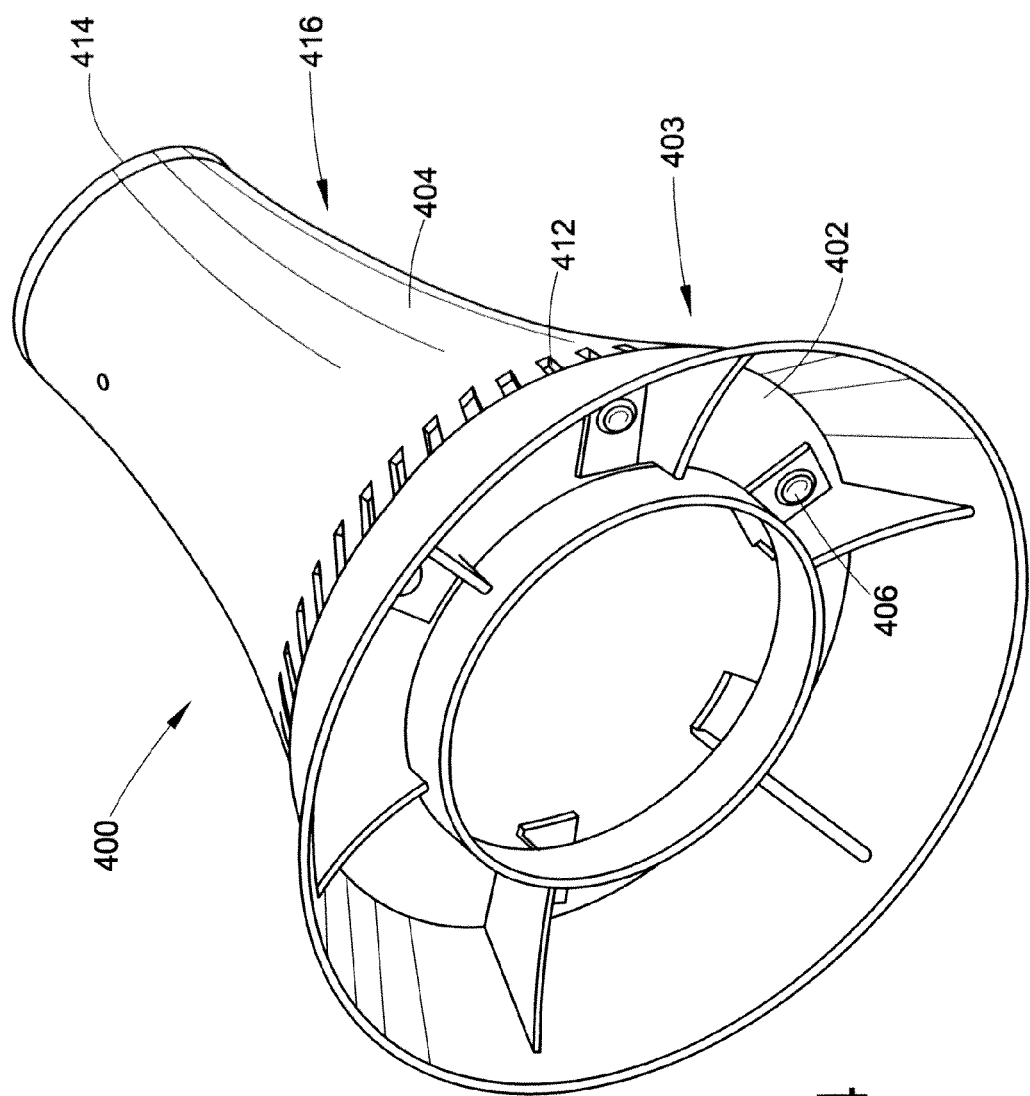
FIG. 4 is a schematic view of an alternative embodiment of the lighting device.

With reference now to FIG. 4, a schematic view of an alternative lighting device 400 is shown, The lighting device 400 is generally similar in structure to the device 100 shown in FIG. 1 and operates in a similar manner. The differences between the lighting devices (100, 400) will be described in greater detail below. For example, the alternative lighting device 400 similarly includes a heat conductive layer and/or a circuit board 402 assembled at the bottom end 403 of a housing or body 404, which generally acts as a chimney, inducing an upward flow of air in the lighting device 400. Generally, as shown in FIG. 4, the body 404 is conical in shape. However, other configurations may be implemented to the extent that they help to provide a chimney effect.

Suitably, one or more LEDs 406 may be mounted on the lower surface of the circuit board 402. The LEDs 406 can be phosphor-coated LEDs, RGB LEDs, monochromatic LEDs, or a combination of phosphor and monochromatic LEDs. The light produced by the LEDs 406 may be used for various types of lighting applications, including task lighting, accent lighting, general lighting and/or horticultural lighting. The system may provide a minimum of 50 lumens and a maximum of 20000 lumens, but preferably between 600 and 10000 lumens.

The lighting device 400 also includes one or more auxiliary LEDs (not shown) mounted on the upper side of the circuit board 402. The auxiliary LEDs generally have an emission that is greater than 400 nm and is preferably at 405 nm (violet) or 450-460 nm (blue). In the case of a transparent conical member or in indirect lighting applications, the LEDs can be white LEDs with a high 405 nm component.

The conical member 404 typically includes at least one outlet opening (not shown) at the upper end and a plurality of small openings (or apertures) 412 spaced radially near the bottom end 403 of the conical member 404. For example, as shown in FIG. 4, the inlet openings 412 may be generally rectangular openings oriented diagonally around the bottom end of the conical member 404. However, other configurations may be implemented to the extent that they help to provide a chimney effect.

As with the lighting device 100 of FIG. 1, the LEDs of the alternative lighting device 400 generate heat during operation. Ambient air is drawn in through the inlet openings 412. The heated air flows upwards and out through an opening 414 at the top end 416 of the conical member 404.

The air stream within the conical member 404 is preferably in contact with a photocatalytic layer (not shown) coated on the interior surface of the conical member 404. The photocatalytic layer is substantially similar to the one described earlier. In particular, the activated photocatalytic layer suitably oxidizes harmful organic molecules (VOCs) and destroys microbes in the air.

Figure 5:
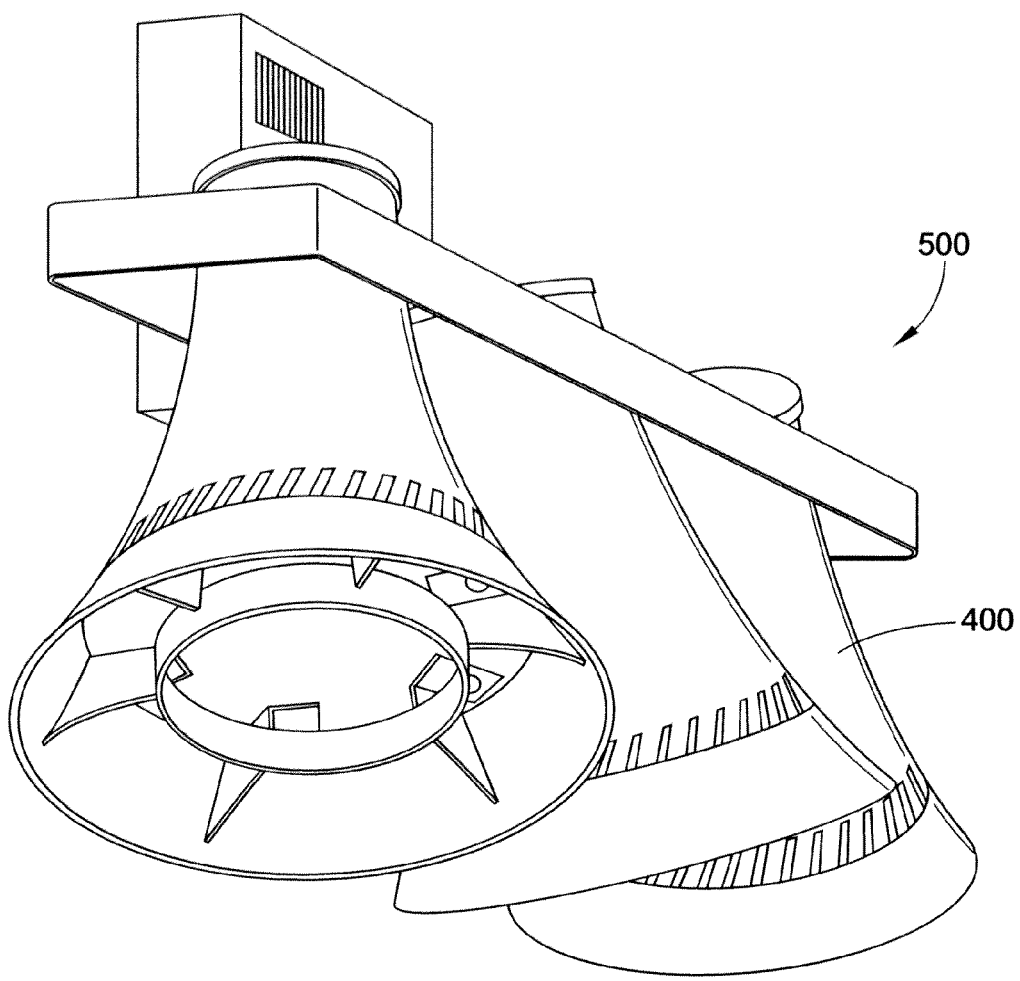
FIG. 5 is a perspective view of the lighting device incorporated into a table lamp.
Figure 6:
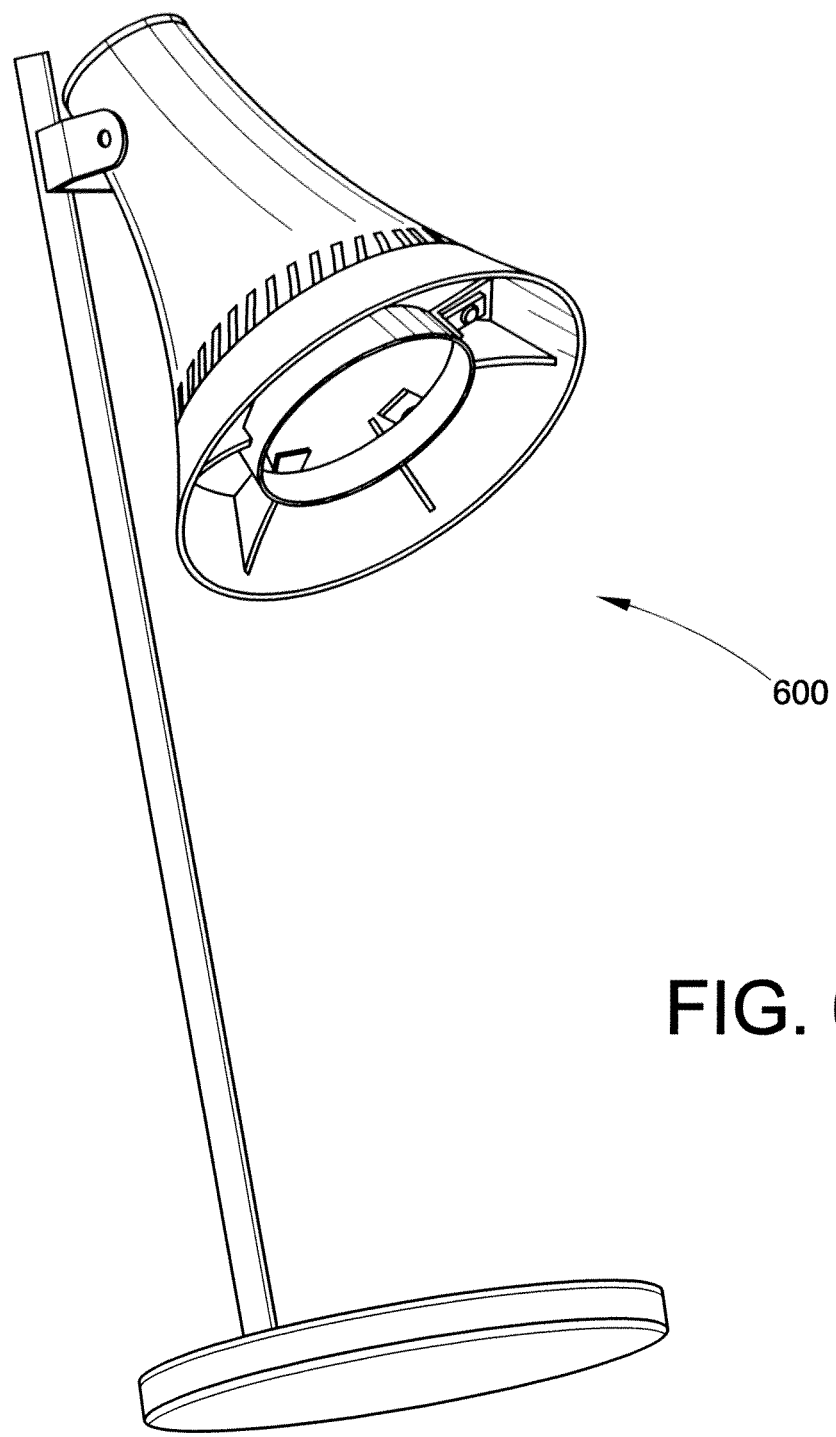
FIG. 6 is a perspective view of the lighting device incorporated into a spot lamp fixture.

FIG. 5 illustrates a table lamp 500 incorporating the lighting device 400. FIG. 6 illustrates a fixture structure 500 incorporating the lighting device 400 for replacing spot lamps. It is to be understood that the lighting device 100 of FIG. 1 would work equally as well in these two configurations.

Figure 7:
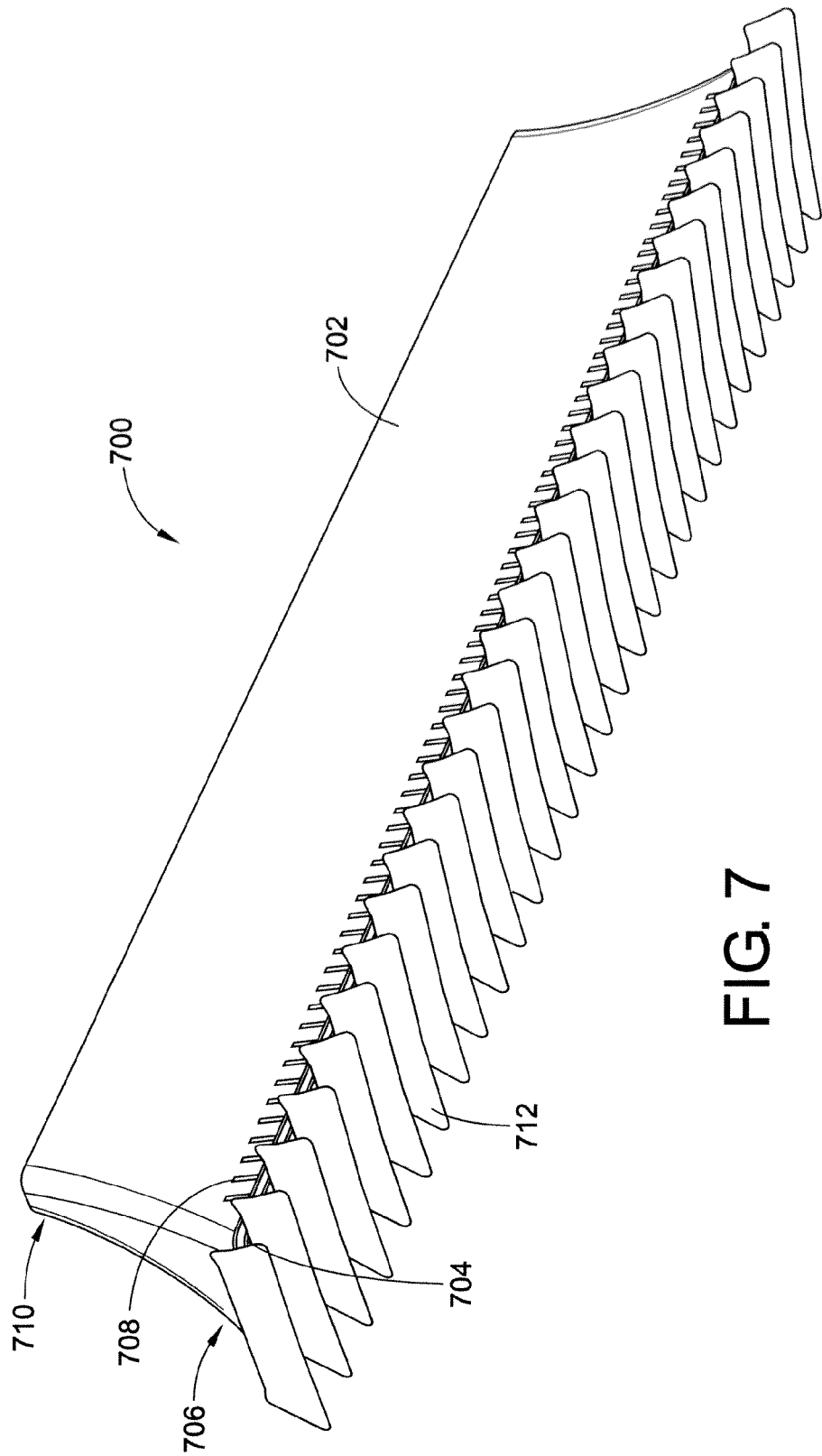
FIG. 7 is a schematic view of a linear lighting device in accordance with the exemplary embodiments.

FIG. 7 shows a linear lighting device 700 with an air purification feature. The linear lighting device 700 includes a housing 702, a first set of LEDs 704 for general lighting applications at the bottom end 706 of the housing 702, a second set of LEDs (not shown) inside the housing 702 for air purification, a plurality of inlet openings 708 near the bottom end 706 of the housing 702 for drawing in ambient air, at least one air outlet opening (not shown) running along the top end 710 of the housing 702, a photocatalytic layer (not shown) on the inner surface of the housing 702, and optical elements 712 along the bottom of the housing 702 for directing light from the first set of LEDs 704. The linear lighting device 700 can replace linear fluorescent lighting fixtures, for example.

Figure 8:
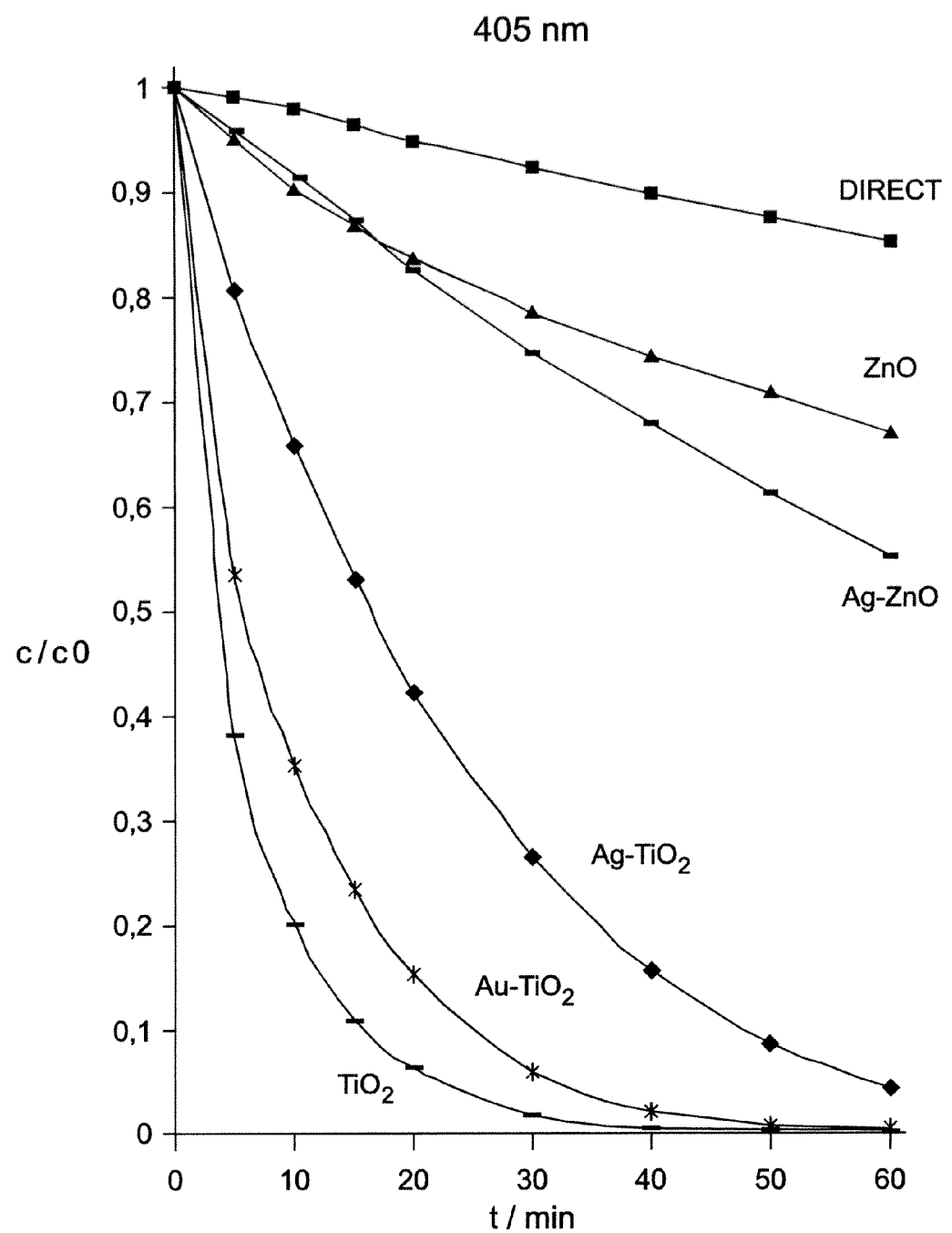
FIG. 8 is graph showing test results for a 405 nm light source and an uncoated test surface (direct), and test surfaces coated with undoped (TiO2) and nano-Ag doped titania coatings.

FIG. 8 shows the results obtained in a reactor containing a 405 nm light source and an uncoated test surface (direct), along with test surfaces coated with undoped ($TiO_2$) and nano-Ag doped titania coatings. In the closed reactor air containing initial 0.35 mmol/liter ethanol vapor was circulated, and the relative ethanol concentration was analyzed by means of gas chromatography and then plotted versus time.

The air flow needed to effectively purify the air when using blue wavelength is approximately 0.3 W@405 nm/$m^3$. This value is also in line with a common practice of using 254 nm UV air purification (0.15 W/$m^3$).

The amount of time needed to cycle through all of the air in a typical conference, hotel, or hospital room is approximately three hours in a room having a height of three meters. Factors such as room temperature, artificial ventilation, and/or distance from ceiling may affect the overall performance of the device. With a constant light "ON" a significant reduction in pollutants is expected.

Figure 9:
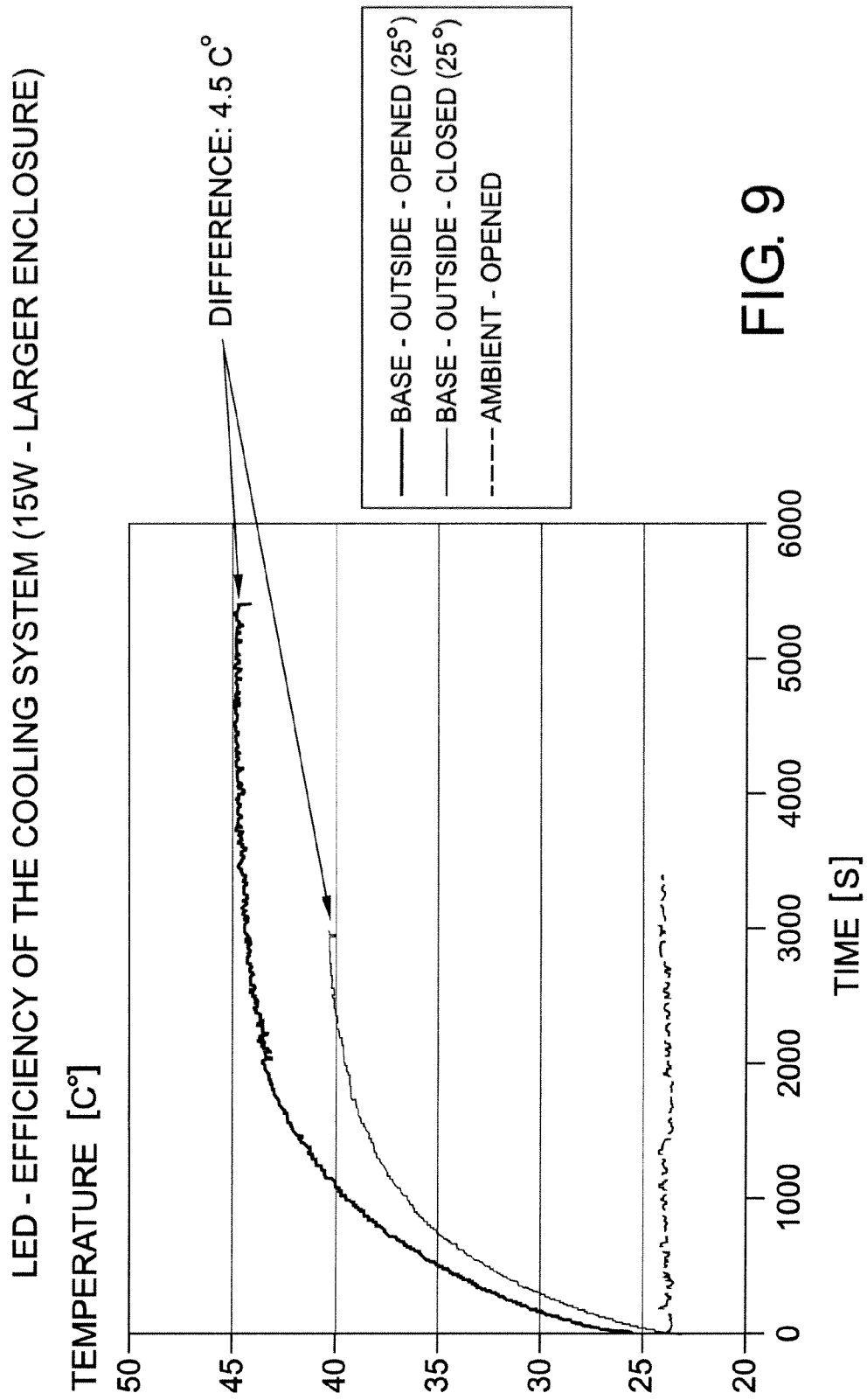
FIG. 9 is a graph showing the efficiency of the cooling system for a 15 W—larger enclosure lighting device.
Figure 10:
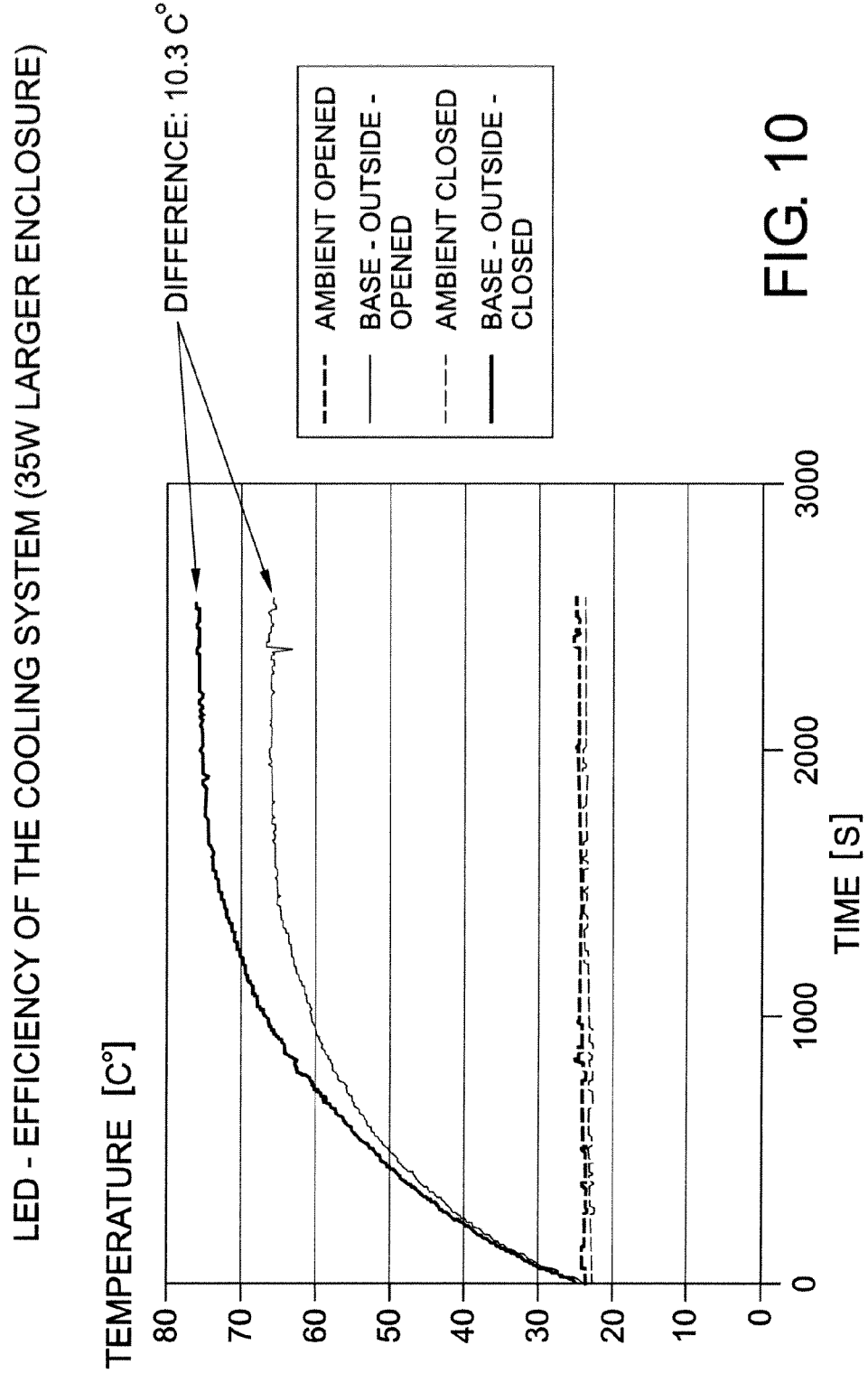
FIG. 10 is a graph showing the efficiency of the cooling system for a 35 W larger enclosure lighting device.
Figure 11:
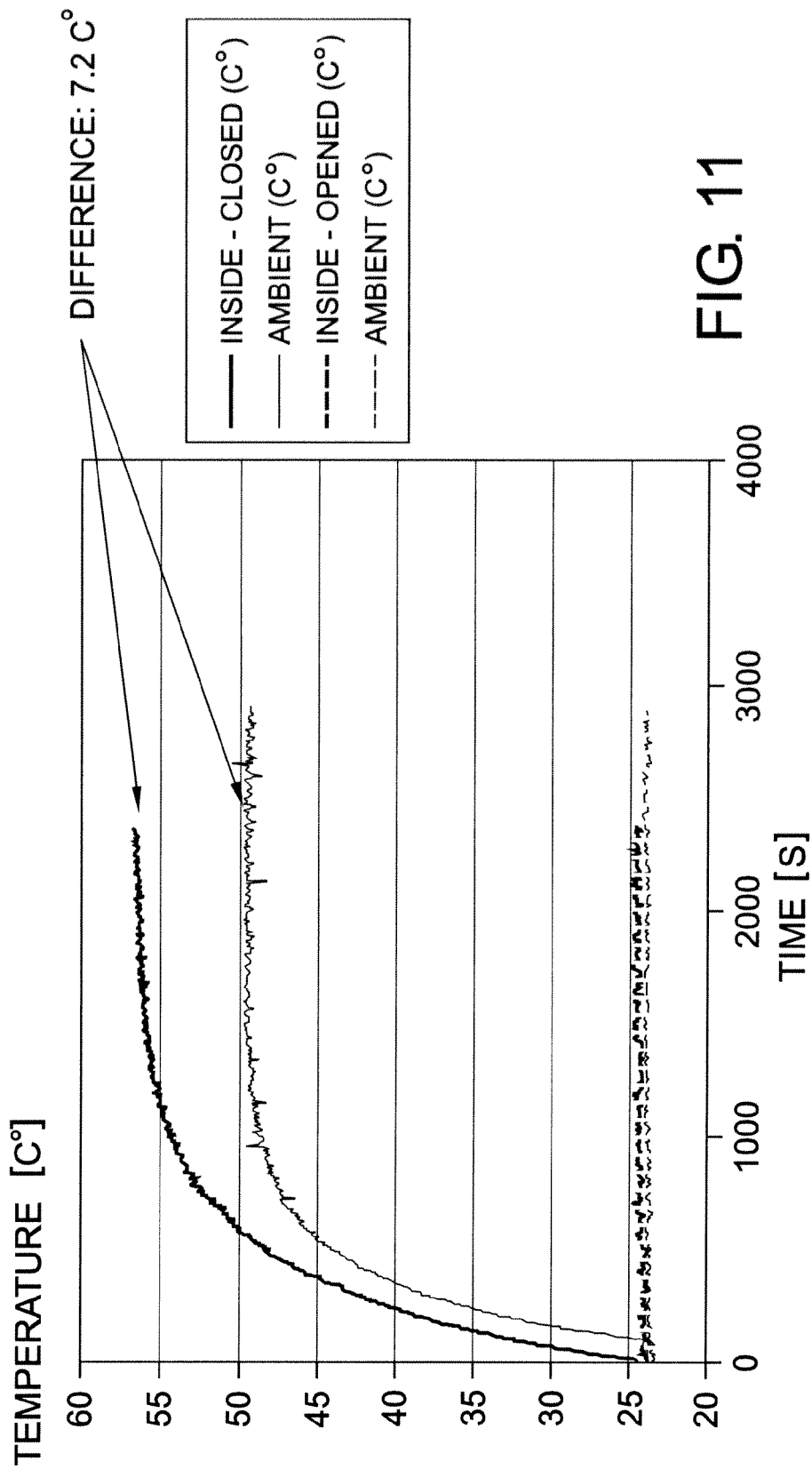
FIG. 11 is a graph showing the efficiency of the cooling system for a 14 W smaller enclosure lighting device.

With reference to FIGS. 9-11, the exemplary embodiment has been tested to confirm that the natural ventilation works. In particular, the temperature of the circuit board 102 of the lighting device 100 was first measured with the inlet holes 112 open. Next, the inlet holes 112 on the bottom were closed so that there was no convection on the fixture. When comparing the two results, it is evident that in case of the closed holes, the temperature is higher. See, for example, the graphs shown in FIG. 9 (15 W—larger enclosure), FIG. 10 (35 W—larger enclosure), and FIG. 11 (14 W—smaller enclosure). The shape of the device 100 may differ with respect to the diameters of the upper and lower sides, the height, however, is generally the same.

Figure 12:
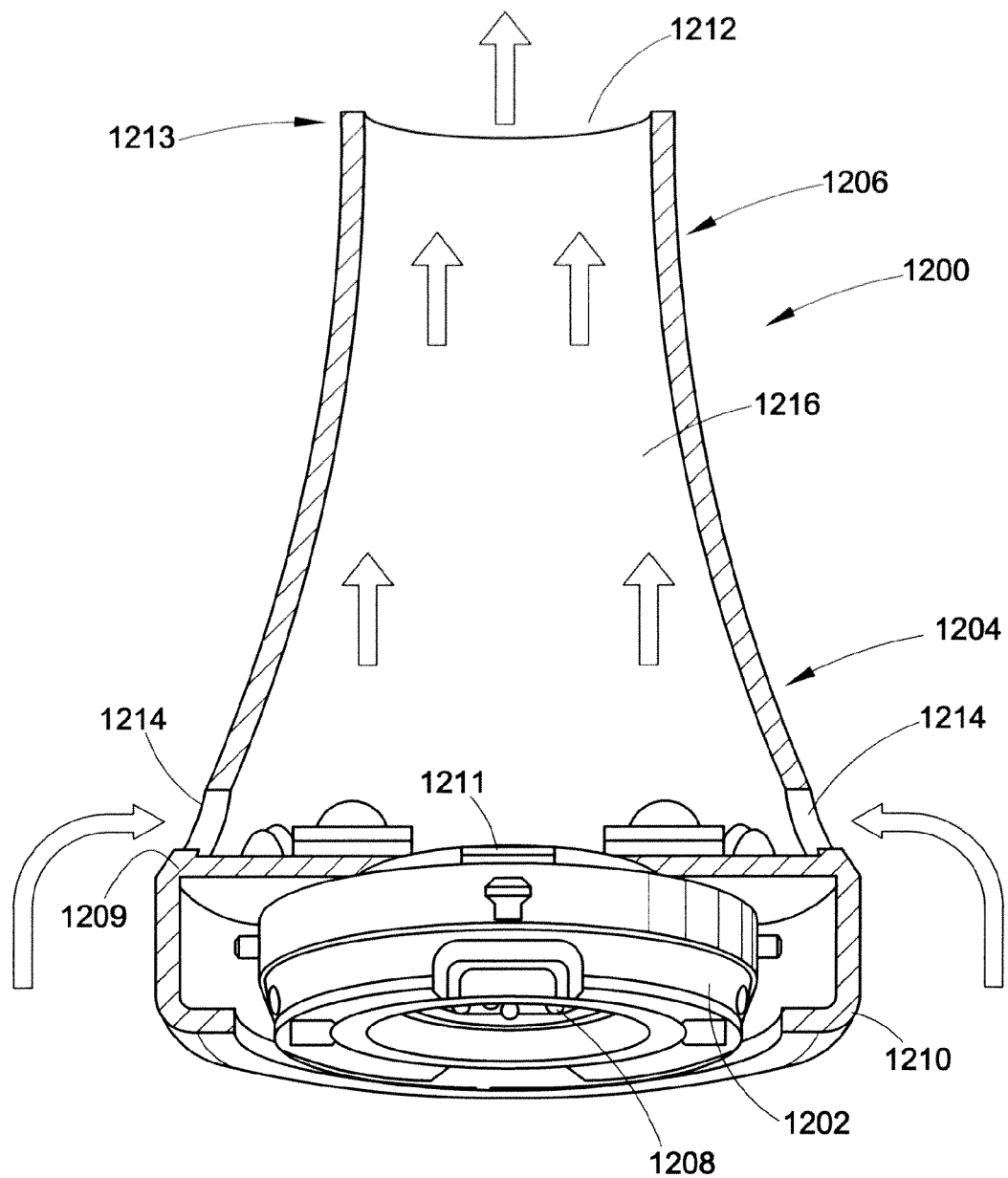
FIG. 12 is a schematic view of another embodiment of the lighting device.

With reference now to FIG. 12, a schematic view of an alternative lighting device 1200 is shown. The lighting device 1200 is generally similar in structure to the device 100 shown in FIG. 1 and operates in a similar manner. The differences between the lighting devices (100, 1200) will be described in greater detail below. For example, the alternative lighting device 1200 includes an LED module 1202 removably thermally and electrically coupled to the bottom end 1204 of a housing or body 1206, which generally acts as a chimney, inducing an upward flow of air in the lighting device 1200. Generally, as shown in FIG. 12, the body 1206 is conical in shape. However, other configurations may be implemented to the extent that they help to provide a chimney effect.

Suitably, one or more LEDs 1208 may be mounted on the lower surface of the module 1202. The LEDs 1208 can be phosphor-coated LEDs, RGB LEDs, monochromatic LEDs, or a combination of phosphor and monochromatic LEDs. The light produced by the LEDs 1208 may be used for various types of lighting applications, including task lighting, accent lighting, general lighting and/or horticultural lighting. In addition, one or more optical elements may be included. The system may provide a minimum of 50 lumens and a maximum of 20000 lumens, but preferably between 600 and 10000 lumens.

The lighting device 1200 also includes one or more auxiliary LEDs (not shown) mounted on the upper side of a heat conductive layer 1209 on a mechanical holder 1210 for the module 1202. The mechanical holder 1210 provides mechanical and electrical connection of the module 1202 to the housing 1206. Generally, the LED module 1202 includes a thermal pad 1211. The thermal pad 1211 provided with the module 1202 generally creates improved thermal connection with the heat conductive layer 1209 so as to increase the chimney effect. An example of an LED module for use in a lighting assembly is described, for example, in US Pub. No. 2011/0063849, the disclosure of which is incorporated herein by reference.

The auxiliary LEDs generally have an emission that is greater than 400 nm and is preferably at 405 nm (violet) or 450-460 nm (blue). In the case of a transparent conical member or in indirect lighting applications, the LEDs can be white LEDs with a high 405 nm component.

The housing 1206 typically includes at least one outlet opening 1212 at the upper end 1213 and a plurality of small openings (or apertures) 1214 spaced radially near the bottom end 1204 of the housing 1206. For example, as shown in FIG. 12, the small openings 1214 may be generally circular. However, other configurations may be implemented to the extent that they help to provide a chimney effect. For example, the small openings 1214 may comprise rectangular openings oriented diagonally around the bottom end of the conical member 404.

As with the lighting device 100 of FIG. 1, the LEDs of the alternative lighting device 1200 generate heat during operation. Ambient air is drawn in through the inlet openings 1214. The heated air flows upwards and out through the opening 1212 at the top end 1213 of the housing 1206.

The air stream within the housing 1206 is preferably in contact with a photocatalytic layer 1216 coated on the interior surface of the housing 1206. The photocatalytic layer 1216 is substantially similar to the one described earlier. In particular, the activated photocatalytic layer suitably oxidizes harmful organic molecules (VOCs) and destroys microbes in the air.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A lighting and air purification apparatus comprising:
   a body having a top end and a bottom end and an interior surface coated with a photocatalytic layer for purifying air, wherein the body also includes a plurality of inlet openings spaced near the bottom end configured to draw in ambient air and at least one outlet opening at the top end configured to release heated air;
   a heat conductive element at the bottom end of the body; and a first set of LEDs on a lower surface of the heat conducting element and a second set of LEDs on an upper surface of the heat conducting element, wherein the first set of LEDs is configured to provide light and the second set of LEDs is configured to provide light having an emission that is greater than 400 nm for air purification.

2. The apparatus of claim 1, wherein the body comprises a conical member and the top end of the conical member has an upper diameter that is smaller than a lower diameter of the bottom end of the conical member.

3. The apparatus of claim 2, wherein the outlet opening comprises a round hole and the inlet openings comprise round holes spaced radially around the bottom end of the conical member.

4. The apparatus of claim 2, wherein the outlet opening comprises a round hole and the inlet openings comprise rectangular openings oriented diagonally and spaced radially around the bottom end of the conical member.

5. The apparatus of claim 1, wherein the first set of LEDs are configured to provide light between 50 and 20000 lumens.

6. The apparatus of claim 1, wherein the thickness of the photocatalytic layer is configured to allow transmission of visible light.

7. The apparatus of claim 1, wherein the photocatalytic layer comprises doped titanium oxide that is activated by light from the second set of LEDs.

8. The apparatus of claim 1, wherein the photocatalytic layer comprises single or mixed oxides of metals selected from the group of Ti, Zn, Zr, Ce, V, W, Bi—W, W—Cd, Zn—In, Bi—Cd—In, and Pb—Bi—Nb.

9. The apparatus of claim 1, wherein the photocatalytic layer comprises an oxide-nitride compositions selected from the group of GaN—ZnO and $Ge_3N_4$—$RuO_2$.

10. The apparatus of claim 1, wherein the photocatalytic layer is configured to oxidize harmful organic molecules (VOCs) and destroy microbes in the ambient air drawn in through the inlet openings.

11. The apparatus of claim 1, wherein the heat conductive element comprises a metal plate, wherein each set of LEDs is attached by screws.

12. The apparatus of claim 1, wherein the heat conductive element comprises a metal plate, wherein each set of LEDs is attached by metal bonding.

13. The apparatus of claim 1, wherein the heat conductive element comprises a heat conductive plate with a metal core printed circuit board attached to each side, wherein the metal core printed circuit board on the bottom side is substantially as large as the heat conductive plate and the metal core printed circuit board on the inner side is smaller than the heat conductive plate for creating a heat bridge between the heat conductive plate and air moving inside the body.

14. The apparatus of claim 1, wherein the body comprises a conical member that is transparent and the second set of LEDs are white LEDs with a high component in the range of 400-500 nm.

15. The apparatus of claim 1, further comprising one or more optical elements at the bottom end of the body that are configured to direct light from the first set of LEDs.

16. The apparatus of claim 1, wherein the body comprises a linear member and includes one or more optical elements that are configured to direct light from the first set of LEDs.

17. A pendant luminaire incorporating the apparatus of claim 1.

18. A table lamp incorporating the apparatus of claim 1.

19. A lighting and air purification apparatus comprising:
a body having a top end and a bottom end and an interior surface coated with a photocatalytic layer for purifying air, wherein the body also includes a plurality of inlet openings spaced near the bottom end configured to draw in ambient air and at least one outlet opening at the top end configured to release heated air;
a mechanical holder at the bottom end of the body that is configured to provide mechanical and electrical connection of an LED module to the body;
a first set of LEDs mounted within the LED module, wherein the first set of LEDs is configured to provide light directed in a downward direction; and
a second set of LEDs mounted on an upper surface of a heat conducting element, wherein the second set of LEDs is configured to provide light directed in an upward direction and having an emission that is greater than 400 nm for air purification.

20. The apparatus of claim 19, wherein the body comprises a conical member and the top end of the conical member has an upper diameter that is smaller than a lower diameter of the bottom end of the conical member.

* * * * *